(12) United States Patent
Yuen

(10) Patent No.: US 7,641,629 B2
(45) Date of Patent: Jan. 5, 2010

(54) BREAST PUMP

(75) Inventor: Yat Keung William Yuen, Hong Kong (CN)

(73) Assignee: Sea Profit (Hong Kong) Limited, Kowloon (HK)

( * ) Notice: Subject to any disclaimer, the term of this patent is extended or adjusted under 35 U.S.C. 154(b) by 911 days.

(21) Appl. No.: 10/821,924

(22) Filed: Apr. 12, 2004

(65) Prior Publication Data
US 2005/0228342 A1  Oct. 13, 2005

(51) Int. Cl.
*A61M 1/06* (2006.01)

(52) U.S. Cl. .......................... 604/74; 604/73; 604/315; 604/346

(58) Field of Classification Search ............. 604/73–76, 604/35, 36, 132, 133, 346; 450/36–38
See application file for complete search history.

(56) References Cited

U.S. PATENT DOCUMENTS

| | | | |
|---|---|---|---|
| 2,444,257 A | | 6/1948 | Jenner |
| 3,551,069 A | | 12/1970 | Morris, Jr. |
| 4,673,388 A | * | 6/1987 | Schlensog et al. .............. 604/74 |
| 4,883,464 A | * | 11/1989 | Morifuki ..................... 604/74 |
| 4,886,494 A | * | 12/1989 | Morifuji ..................... 604/74 |
| 5,542,921 A | | 8/1996 | Meyers et al. |
| 5,947,923 A | * | 9/1999 | Uehara et al. ................. 604/74 |
| 6,045,529 A | | 4/2000 | Nuesch |
| 6,090,065 A | | 7/2000 | Giles |
| 6,355,012 B1 | | 3/2002 | Nuesch |
| 6,547,756 B1 | * | 4/2003 | Greter et al. .................. 604/74 |
| 6,673,036 B1 | | 1/2004 | Britto |
| 2005/0101908 A1 | * | 5/2005 | Atkin et al. ................... 604/74 |

FOREIGN PATENT DOCUMENTS

| | | |
|---|---|---|
| CN | 2127873 Y | 3/1993 |
| CN | 2141286 Y | 9/1993 |
| CN | 2172649 Y | 7/1994 |
| CN | 2523431 Y | 12/2002 |
| CN | 2580971 Y | 10/2003 |

* cited by examiner

*Primary Examiner*—Nicholas D Lucchesi
*Assistant Examiner*—Quynh-Nhu H Vu
(74) *Attorney, Agent, or Firm*—Buchanan Ingersoll & Rooney PC (57) ABSTRACT

An electric breast pump is disclosed as including a hood to be fitted over a breast of a user, a chamber in fluid communication with the hood member via a one-way valve, a pump motor operatively associated with a pump diaphragm movable to draw air from the hood into the chamber via the valve, in which the chamber has an opening and a lid which is operatively associated with the motor, in which the lid is movable between a first position to close the opening and a second position in which the opening is open, and in which the lid is at the first position when the motor is in operation and is at the second position when the motor is not in operation. The breast pump also includes sensors for detecting the passing of milk, and a microcontroller for calculating the rate of flow of milk on the basis of data received from the sensors.

54 Claims, 13 Drawing Sheets

Fig. 15 ures and function of which will be further discussed below.

BREAST PUMP

This invention relates to a breast pump and, in particular, an electrically operated breast pump for drawing milk from a user.

BACKGROUND OF THE INVENTION

There are in existence a large number of electrically operated breast pumps, allowing a user, e.g. a mother, to pump milk from her breast. Various pumping mechanisms have been proposed for drawing milk from the mother's breast, including, for example, ones disclosed in U.S. Pat. Nos. 6,045,529 and 6,355,012 issued to Nüesch. Such mechanisms are generally speaking rather complicated, and thus costly to manufacture. In addition, most such mechanisms include gear trains which would generate much noise, especially when the motor is operating at a relatively high speed.

In addition, although a user may, with some existing breast pumps, be able to adjust the pumping cycles, e.g. by varying the number of suction cycles per minute, or adjusting the vacuum level for pumping milk from the user's breast, it is up to the user to decide whether to make such variation or adjustment, and the user may simply have no information on which to decide whether the current pumping rate is suitable or not. In this connection, U.S. Pat. No. 6,547,756 issued to Greter et al. discloses a programmable breast pump which may be programmed to generate a number of different milk expression (extraction) sequences, or curves. In this arrangement, a motorized pump is provided with a microprocessor-based controller. Cards, with microprocessor "chips", containing instructions for different suction curves are also included, which may be inserted into the breast pump, so that the instructions in the cards may be read and acted upon by the breast pump. However, as in the case of other adjustable breast pumps discussed above, it is still up to a user to decide whether to change the mode of pumping operation of the breast pump, and a user may not know whether an alternative, and if so which, suction curve should be applied. A further shortcoming associated with conventional electric breast pumps is that the user is provided with no information as to the time required to fill up the milk receptacle, e.g. bottle.

Such and other shortcomings discussed above are also present in breast pumps disclosed in U.S. Pat. No. 6,673,036 issued to Britto and U.S. Pat. No. 6,090,065 issued to Giles.

It is thus an object of the present invention to provide an electric breast pump in which the aforesaid shortcomings are mitigated or at least to provide a useful alternative to the public.

SUMMARY OF THE INVENTION

According to a first aspect of the present invention, there is provided an electric breast pump including at least one hood member adapted to be fitted over a breast of a user; a chamber adapted to be in fluid communication with said hood member via a first valve; a first motor operatively associated with a pumping member which is movable to draw air from said hood member into said chamber via said first valve; said chamber having at least a first opening and a closure member operatively associated with said first motor, wherein said closure member is movable between a first position to close said first opening and a second position in which said first opening is open; and wherein said closure member is at said first position when said first motor is in operation and is at said second position when said first motor is not in operation.

According to a second aspect of the present invention, there is provided an electric breast pump including at least one hood member adapted to be fitted over a breast of a user; and at least a first sensing unit adapted to detect the passing of milk.

BRIEF DESCRIPTION OF THE DRAWINGS

A preferred embodiment of the present invention will now be described, by way of example only, with reference to the accompanying drawings, in which.

DETAILED DESCRIPTION OF THE PREFERRED EMBODIMENT

Figure 1:
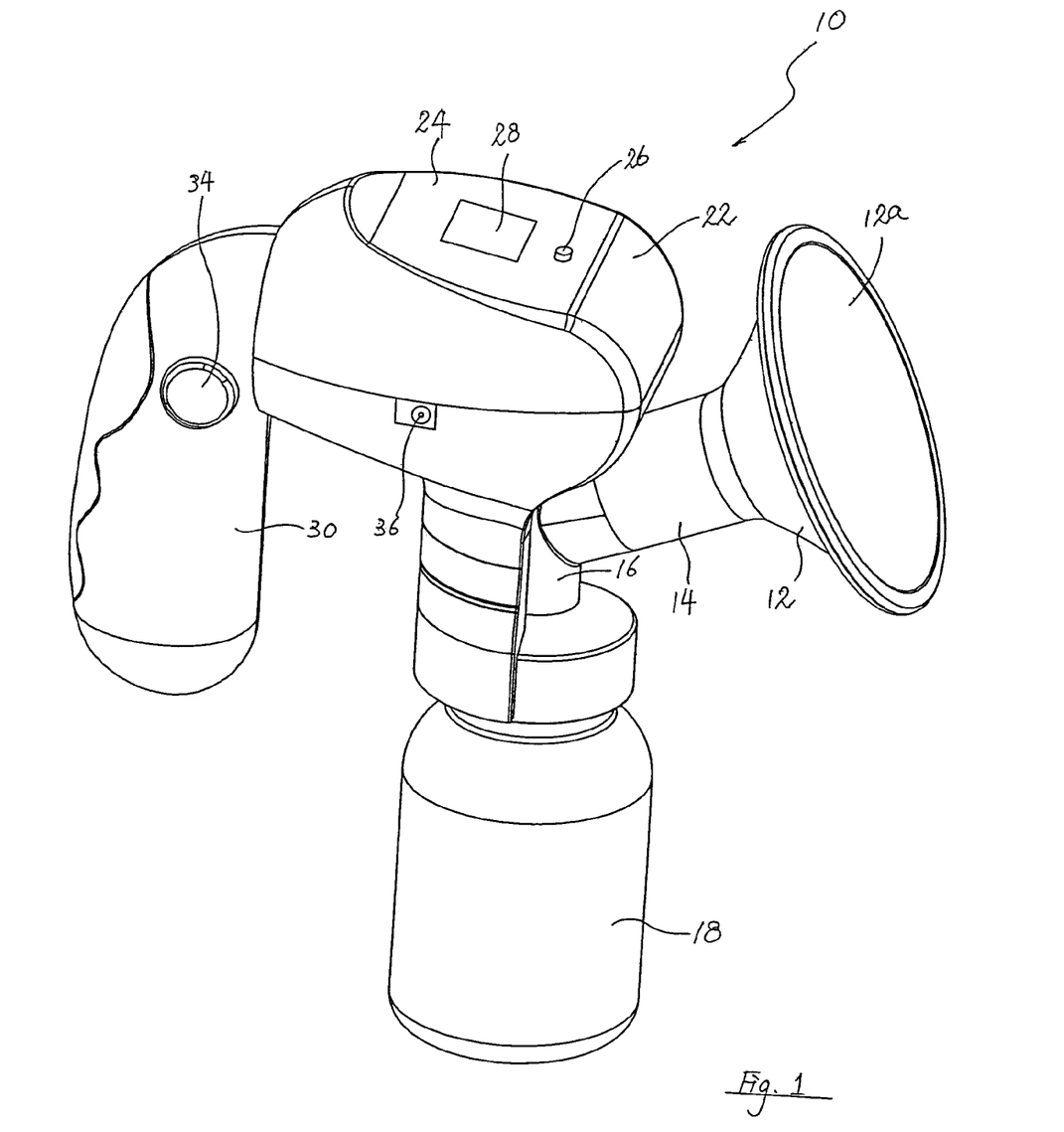
FIG. 1 is a perspective view of an electric breast pump according to the present invention.
Figure 2:
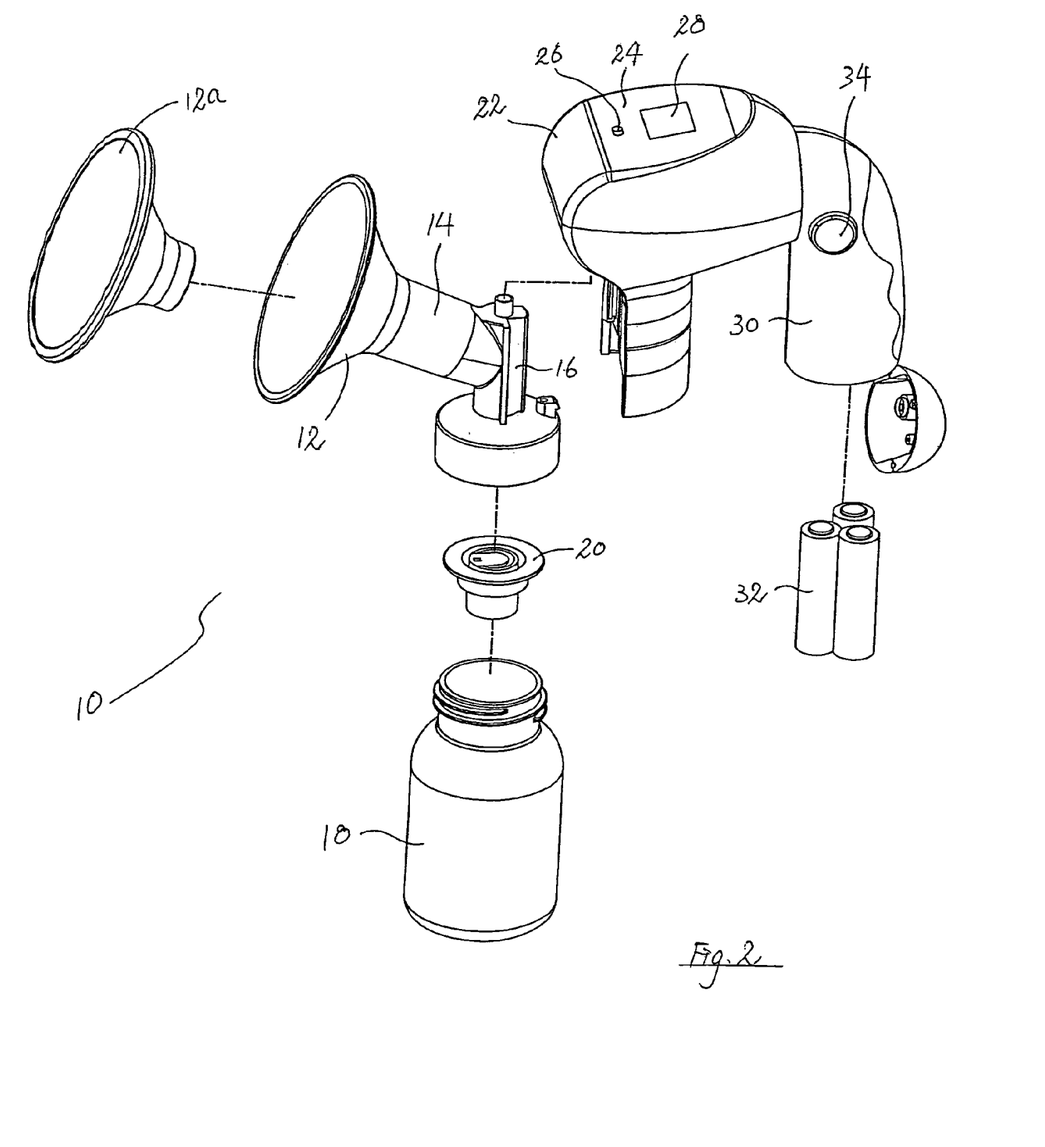
FIG. 2 is an exploded view of the breast pump shown in FIG. 1.

FIGS. 1 and 2 show an electrically operated breast pump according to a preferred embodiment of the present invention, generally designated as 10. The breast pump 10 has a hood 12 adapted to be fitted over a breast of a user in an essentially gas-tight manner, for pumping milk from the breast. An insert 12*a* for contacting the user's breast is received within the hood 12. The insert 12*a* is made of a soft plastic material, e.g. silicone, to provide comfort to the user during use. The hood 12 is in funnel shape and has a tunnel 14 leading to a connector 16, which fluidly communicates with the hood 12, and with a milk-receiving bottle 18 via a valve seat 20, the structure and function of which will be further discussed below.

The connector 16 is engaged with a head portion 22 which houses most of the operating components of the breast pump 10, as will be clear from the ensuing discussion. On a top surface 24 of the head portion 22 is provided with an ON/OFF button 26 for selectively activating/deactivating the breast pump 10. Also provided on the top surface 24 of the head portion 22 is a liquid crystal display (LCD) 28 for displaying various operation information and data relating to the operation of the breast pump 10. The head portion 22 is connected with a handle 30, which also acts as a battery compartment for housing a number of batteries 32 for powering the breast pump 10. The handle 30 is swivellable relative to the head portion 22 for easy handling. On each side of the handle 30 is provided a PAUSE button 34, allowing a user to temporarily suspend the operation of the breast pump 10 by pressing the button 34 once, and to resume its operation by pressing the button 34 once again. On a side of the head portion 22 is a power jack 36 which allows the breast pump 10 to be powered by an A/C source, possibly via a transformer (not shown).

Figures 3, 4:
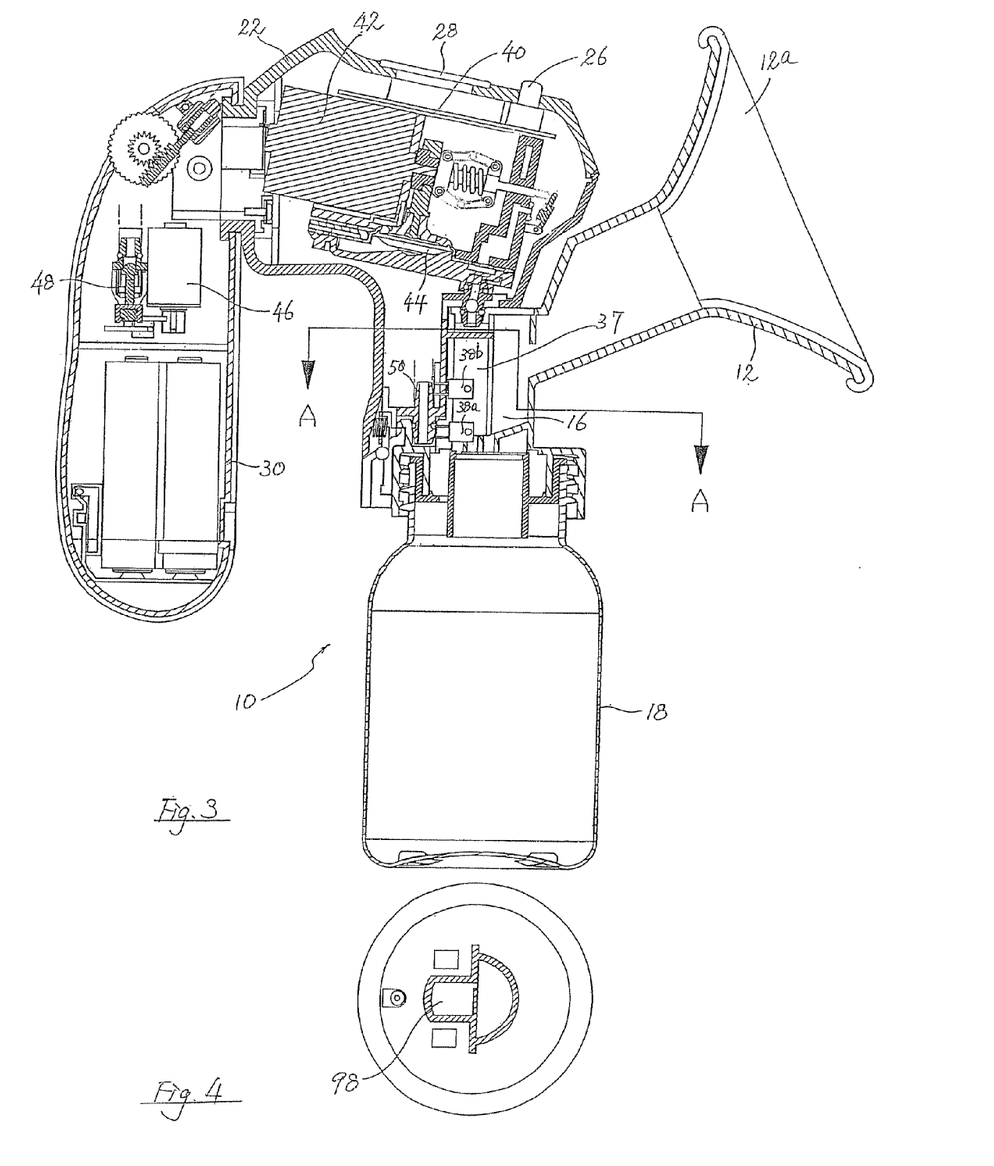
FIG. 3 is a sectional view of the breast pump shown in FIG. 1.
FIG. 4 is a sectional view taken along the line A-A in FIG. 3.

FIG. 3 shows a sectional view of the breast pump 10. As shown in FIG. 3, provided in a chamber 37 of the connector 16 are two infrared (IR) units 38a, 38b, each including an IR transmitter and an IR receiver. Housed in the head portion 22 is a pump motor 42 for operating a pump diaphragm 44 for generating a low pressure (vacuum) in the breast pump 10. Within the handle 30 is a valve motor 46 for operating a needle valve 48. The valve 48 is pneumatically connected, e.g. via a hose (not shown), with a nozzle 50 which is in turn pneumatically connected with the milk-receiving bottle 18.

Figure 5:
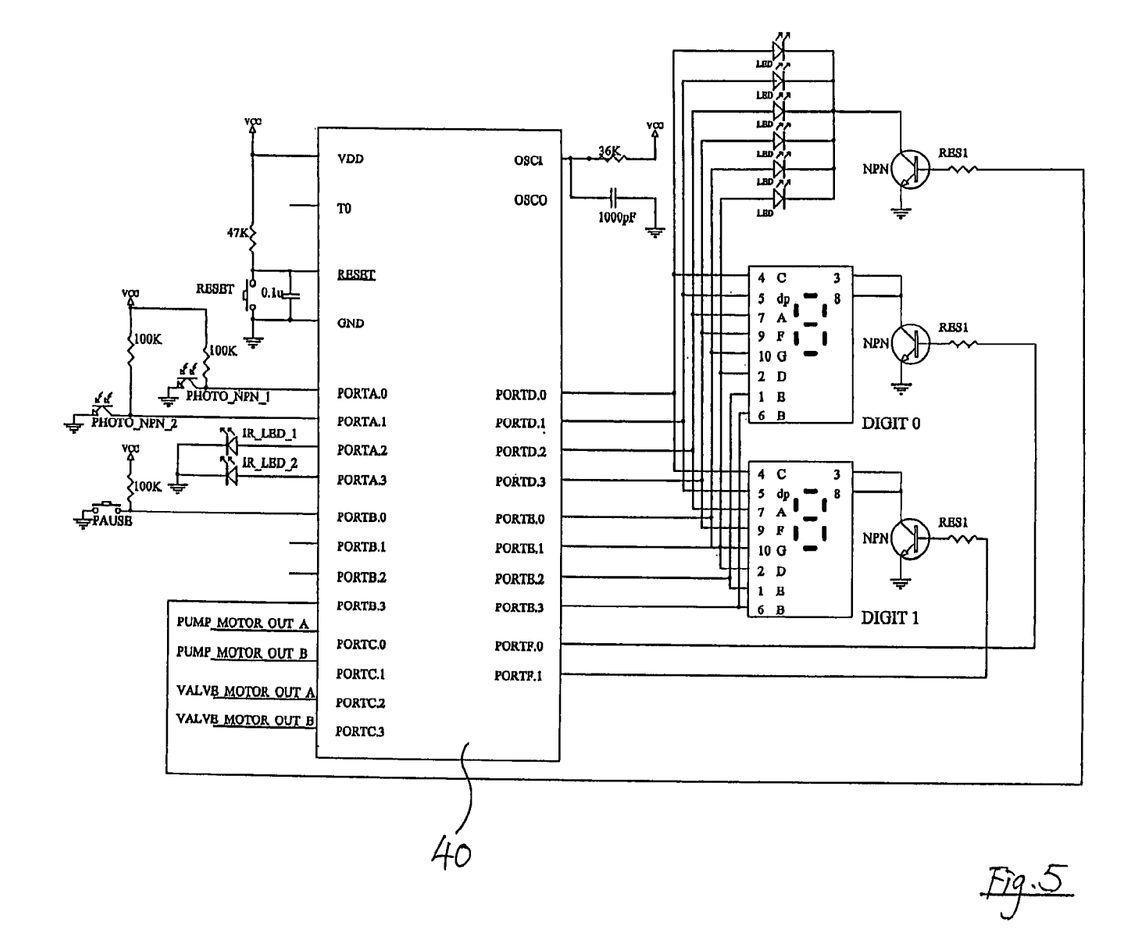
FIG. 5 is a circuit diagram of the breast pump shown in FIG. 1.
Figure 6:
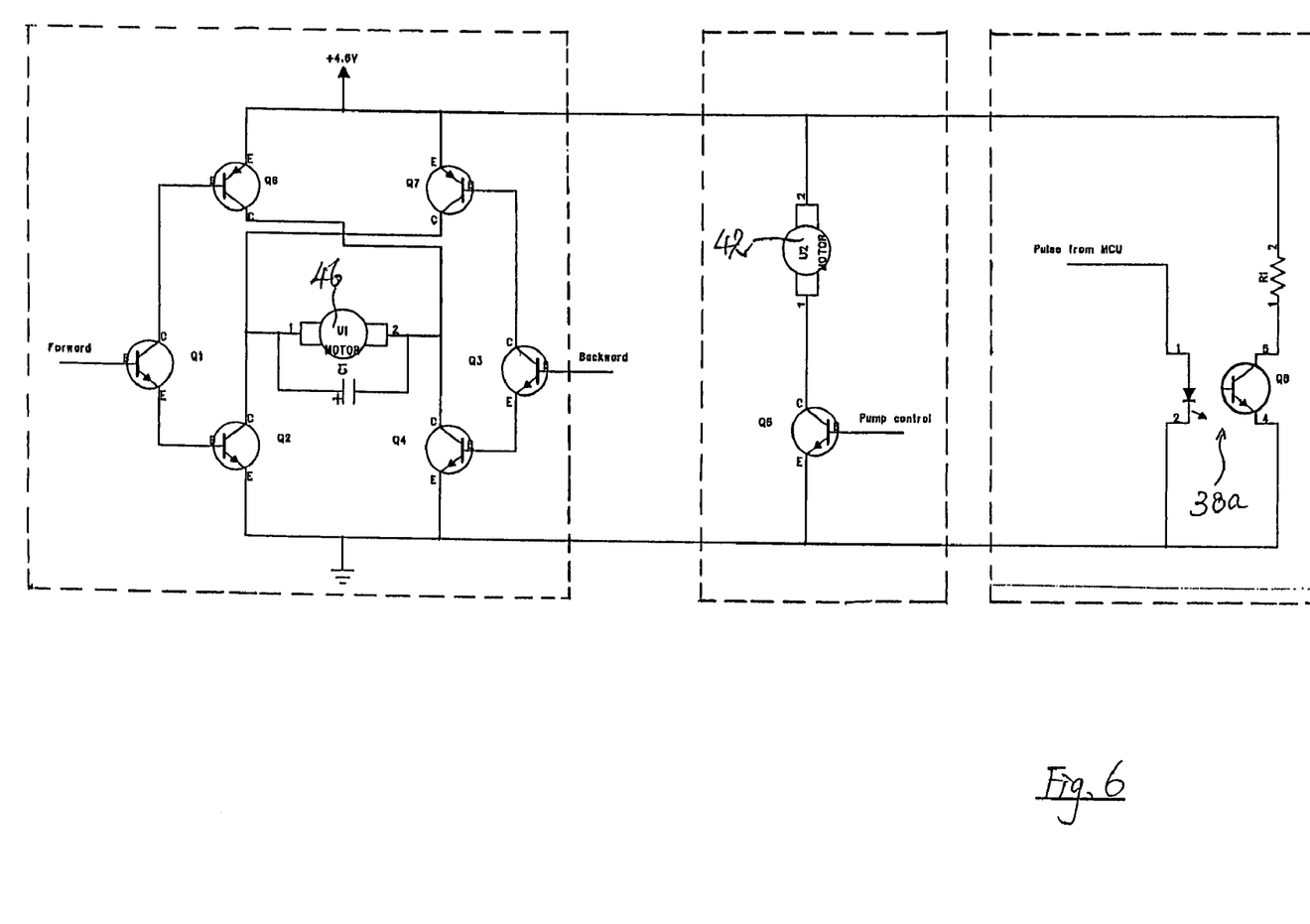
FIG. 6 shows part of the circuitry in the breast pump shown in FIG. 1.

Housed in the head portion 22 is a microcontroller 40 for controlling the operation of various electronic and electrical components of the breast pump 10. As shown in FIG. 5, the microcontrolller 40 is electrically connected with and controls the operation of the pump motor 42, the valve motor 46, and the LCD display 28. The microcontroller 40 is also connected with and receives instructions and/or signals from the PAUSE buttons 34 and the IR units 38a, 38b. FIG. 6 shows in more detail a circuitry which controls the operation of the valve motor 46, the pump motor 42, and the IR units 38a, 38b, of which only one set 38a is shown here.

Figure 7:
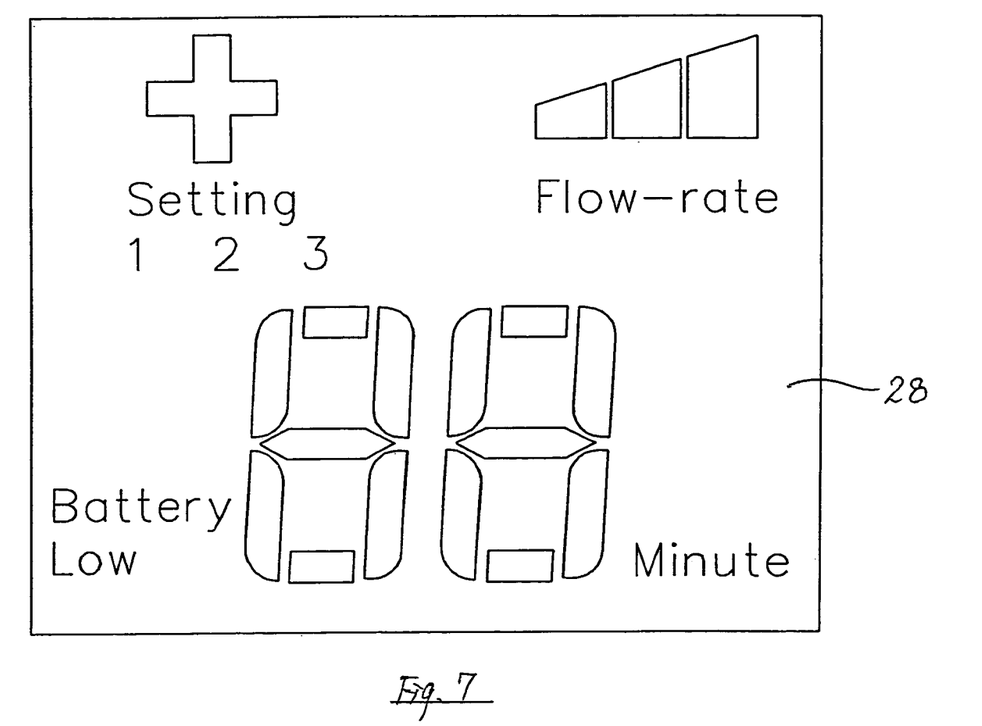
FIG. 7 shows a liquid crystal display (LCD) setting in the breast pump shown in FIG. 1.

FIG. 7 shows the setting of the LCD display 28, and it can be seen that the LCD display 28 may display such information as the setting being used, the flow-rate (slow, medium, high), battery low, and the remaining time (in minutes) required for filling the bottle 18.

Figure 8:
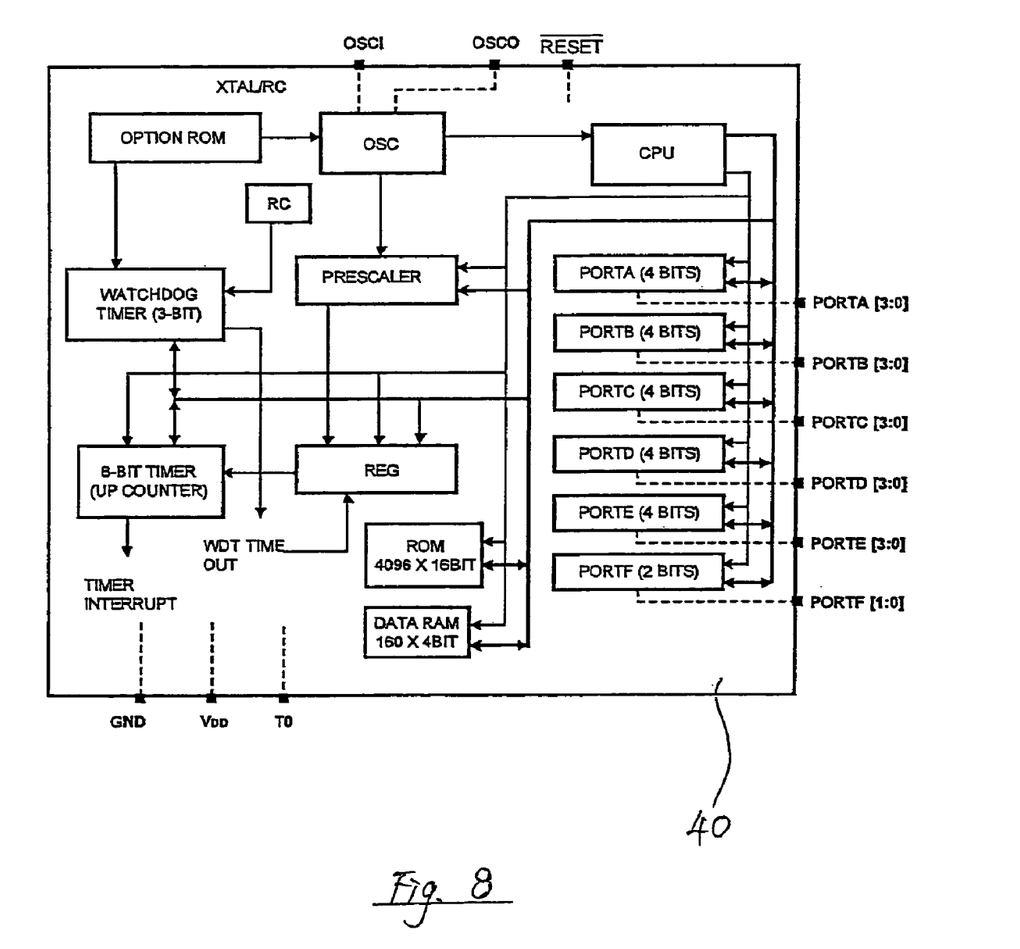
FIG. 8 is a block diagram of an exemplary microcontroller which may be used in the circuit shown in FIG. 5.

A microcontroller 40 suitable for use in the breast pump 10 may be one traded by Sino Wealth Microelectronics Corporation Limited, of Hong Kong, under serial number SH6622A, although other similar microcontrollers may also be used. SH6622A is a 4-bit microcontroller, which integrates a 4-bit CPU core with SRAM, 4K program ROM, timer and I/O Port. FIG. 8 shows a block diagram of SH6622A. The CPU of SH6622A contains the following function blocks: Program Counter, Arithmetic Logic Unit (ALU), Carry Flag, Accumulator, Table Branch Register, Data Pointer (INX, DPH, DPM, and DPL), and Stack.

Figure 9:
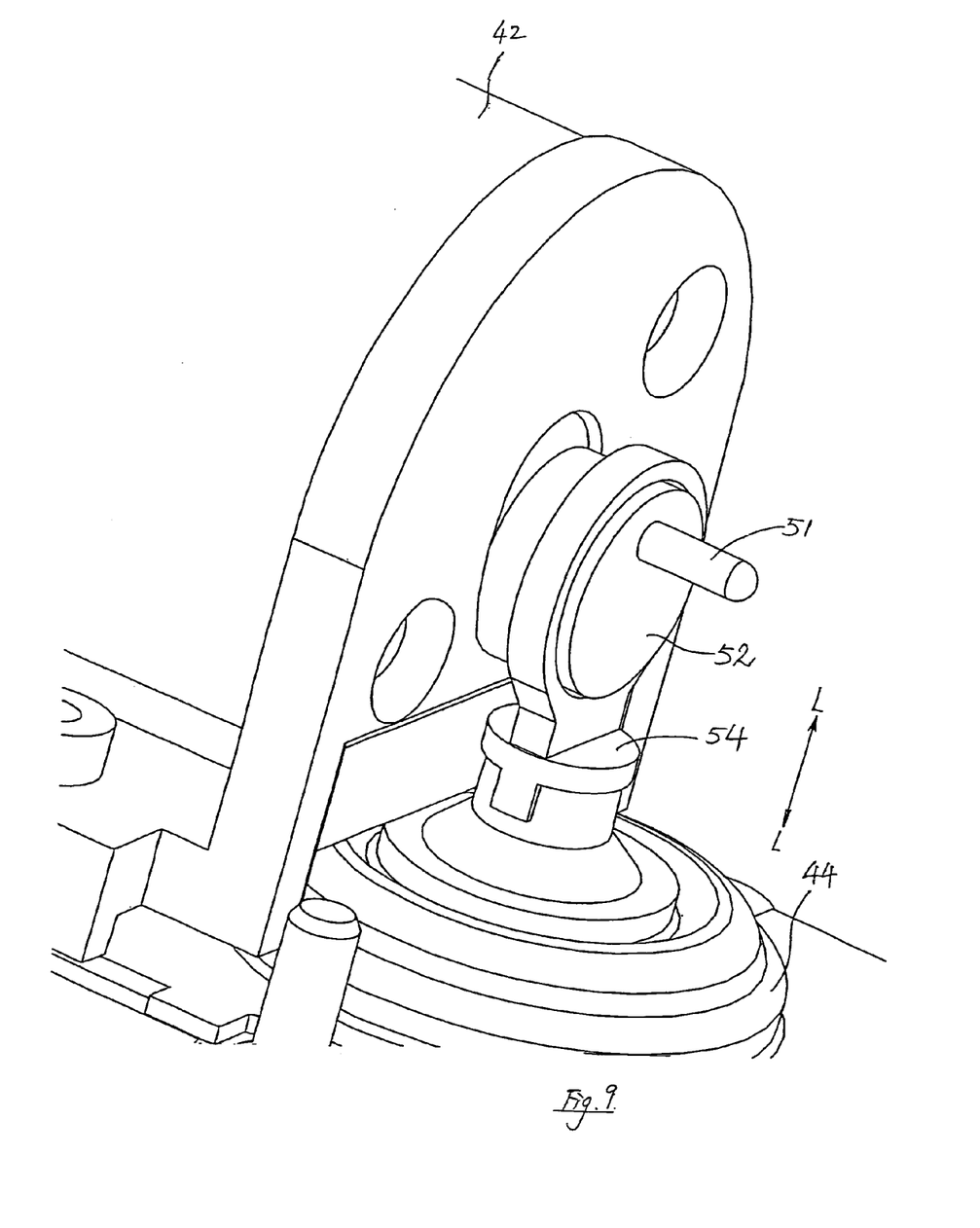
FIG. 9 is an enlarged view showing the engagement between the pump motor and the diaphragm in the breast pump shown in FIG. 1.

FIG. 9 shows an enlarged perspective view of the pump motor 42, having an output spindle 51 engaged with an eccentric cam 52 which in turn carries a yoke 54 fixed with the pump diaphragm 44. By way of such an arrangement, rotational movement of the output pin 51 is converted into linear reciprocal movement of the diaphragm 44 in the direction of the bi-directional arrow L-L.

Figure 10:
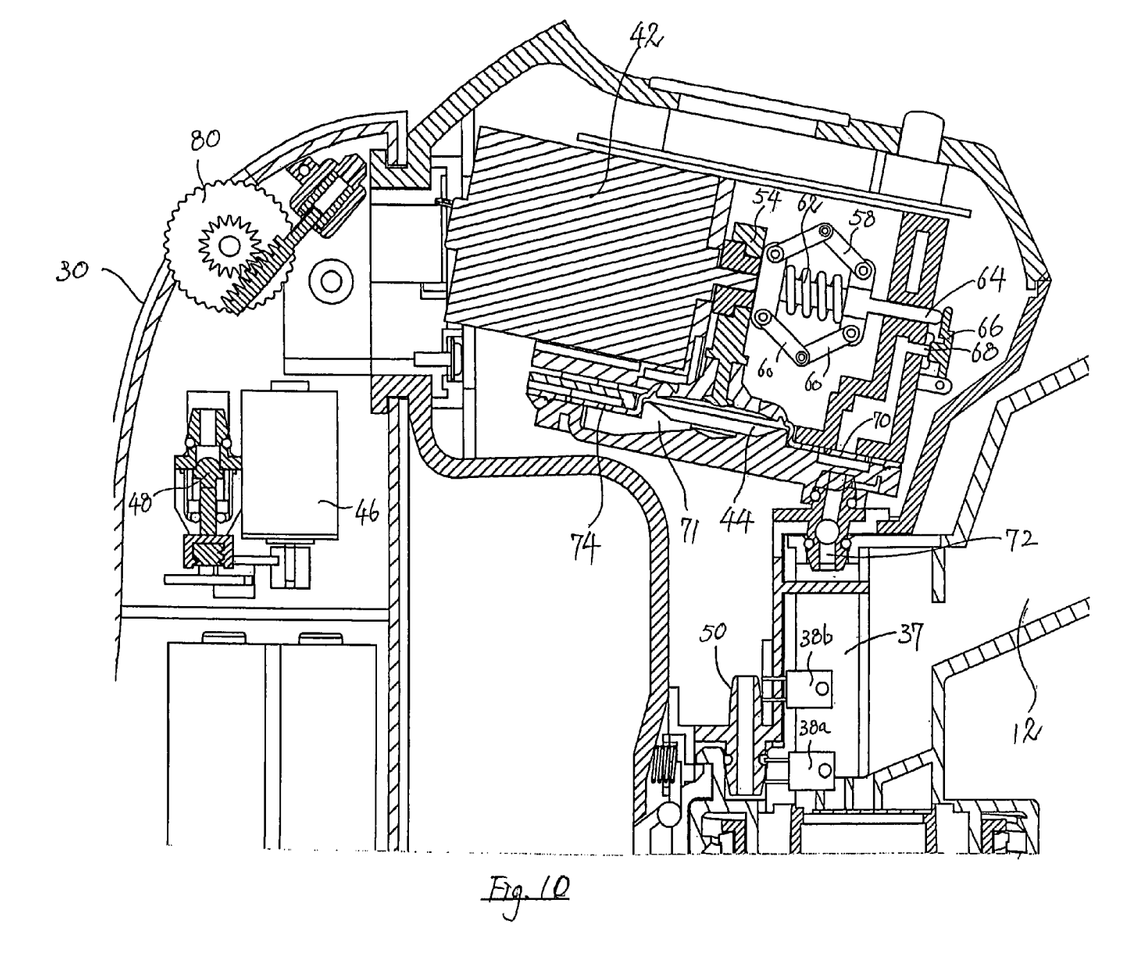
FIG. 10 is an enlarged sectional view of part of the breast pump shown in FIG. 3.

As can be clearly seen in FIG. 10, fixed to the output spindle 51 of the pump motor 42 is a linkage mechanism 58 comprising six links 60 linked with one another in a hexagonal ring-shaped structure. Each link 60 is swivellable relative to two adjacent links 60 to which it is pivotally hinged. Over the output spindle 51 is also provided with a spring 62 which biases an end pin 64 outwardly, which in turn acts on and biases a lid 66 away from a vent hole 68. The diaphragm 44 is positioned in a chamber 71 which is closeable by the lid 66, a first one-way valve 70, and a second one-way valve 74. The first one-way valve 70 only allows air to enter the chamber 71 from a conduit 72, which is in turn in fluid communication with the hood 12. The second one-way valve 74 only allows air to exit the chamber 71.

When the motor 42 is not in operation, the linkage mechanism 58 will be biased by the spring 62 to assume the shape and configuration as shown in FIGS. 3 and 10. During operation of the pump motor 42, rotation of the output spindle 51 will bring about simultaneous and corresponding rotation of the linkage mechanism 58, whereby the hexagonal ring-shaped structure 58 will "flatten" because of the centrifugal force generated by the rotation, thus retracting the end pin 64 against the outward biasing force of the spring 62. The lid 66 will thus close the vent hole 68. With the vent hole 68 closed by the lid 66, linear reciprocal movement of the diaphragm 44 in the direction of the bi-directional arrow L-L will draw air from the hood 12, through the conduit 72 and the first one-way valve 70, into the chamber 71, and push the air out through the second one-way valve 74, thus generating a lower pressure ("vacuum") in the hood 12 relative to the outside atmospheric pressure, and mimicking a sucking action of a baby on a mother's breast. The sucking/releasing cycle is completed by a releasing action when the motor 42 stops rotation. Upon stopping of the motor 42, the linkage mechanism 58 will, under the biasing force of the spring 62, resume the stable shape and configuration as shown in FIGS. 3 and 10, whereupon the lid 66 will be pushed by the end pin 64 away from the vent hole 68, to thereby open the vent hole 68 as shown in FIG. 3. When the vent hole 68 is opened, air will enter the vent hole 68, and then back into the hood 12, thus releasing the "vacuum" in the hood 12.

Figure 11:
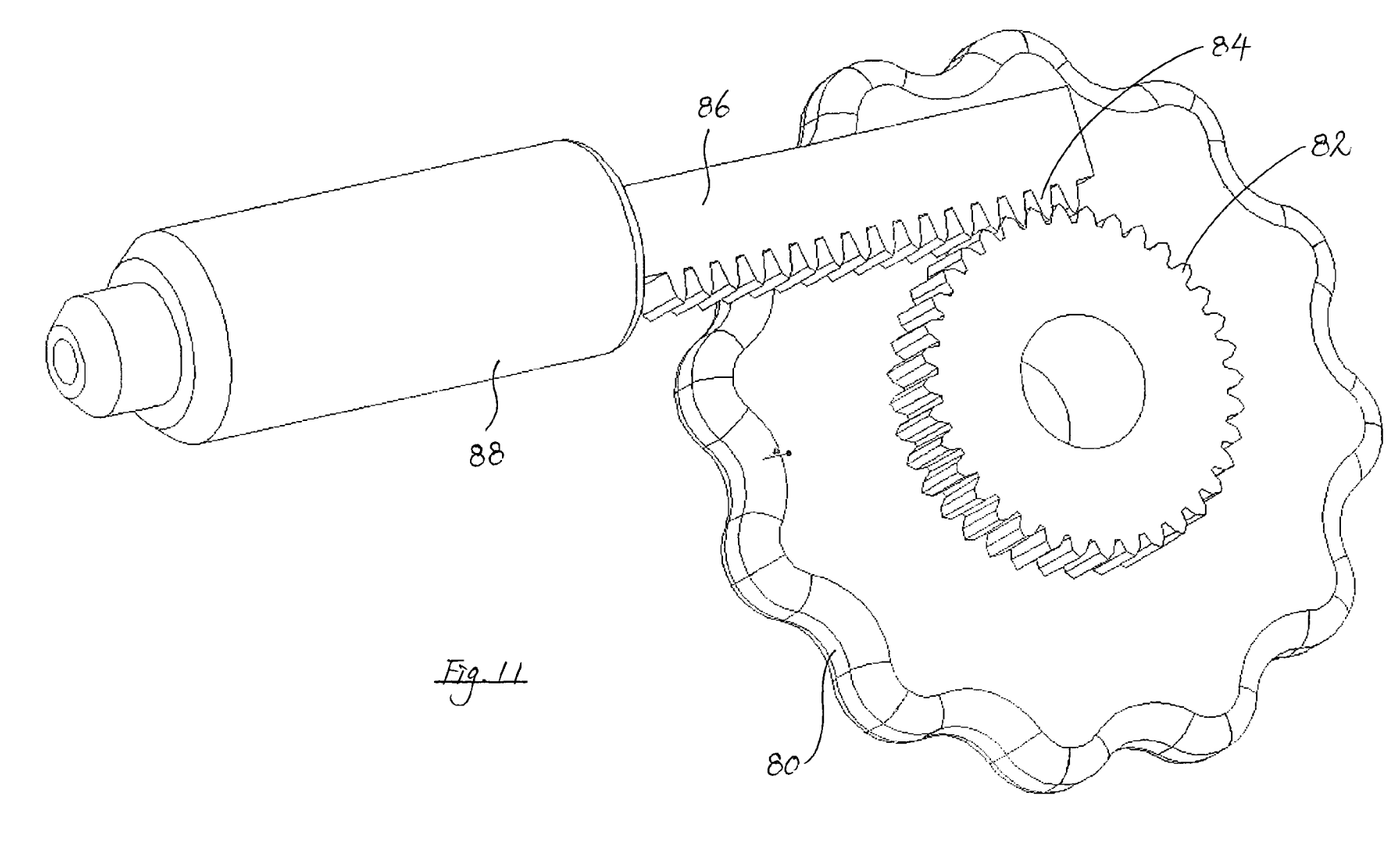
FIG. 11 is an enlarged perspective view showing the mechanism for manual adjustment of the level of vacuum in the breast pump shown in FIG. 1.
Figure 12:
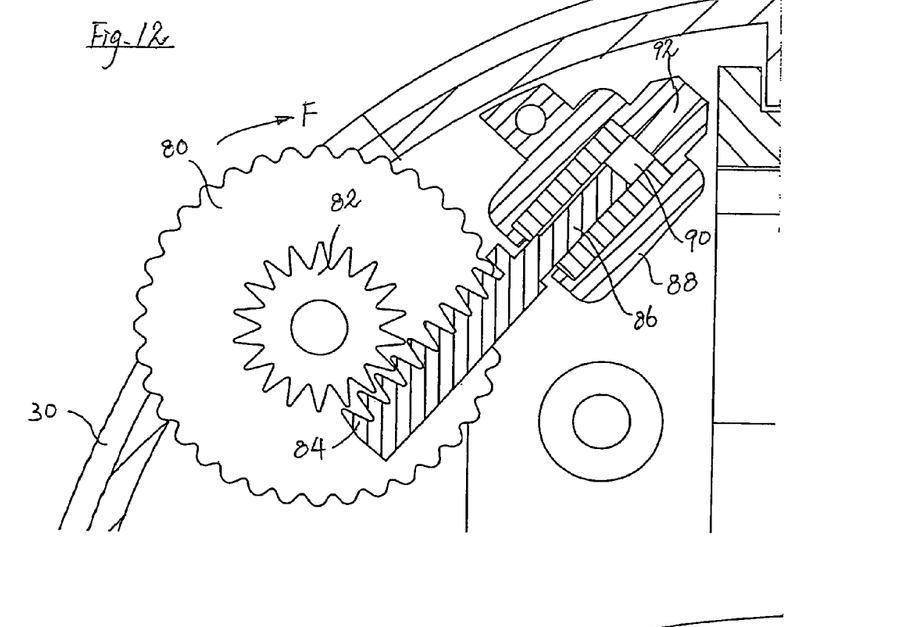
FIG. 12 shows a first configuration of the manual vacuum adjustment mechanism shown in FIG. 11.
Figure 13:
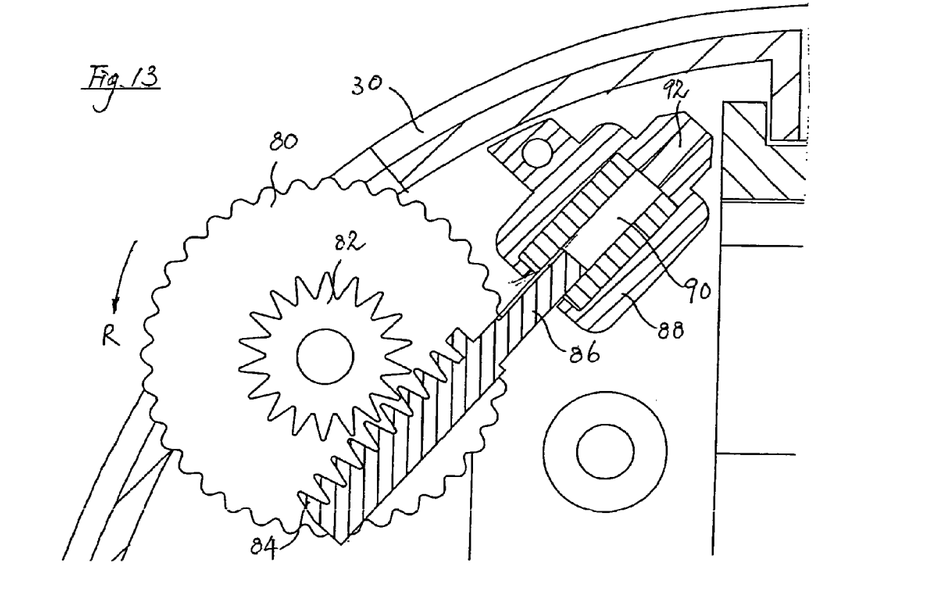
FIG. 13 shows a second configuration of the manual vacuum adjustment mechanism shown in FIG. 11.

To allow further versatility of the breast pump 10, a manual pressure adjustment mechanism is provided, allowing the user to manually adjust the level of "vacuum" applied during operation of the breast pump 10, to suit individual need in different times. As shown in FIG. 11, the manual pressure adjustment mechanism includes a wheel 80 with a gear 82 in mesh with a pinion 84 on an end of a pin 86 and a valve seat 88. As can be seen in FIGS. 10, 12 and 13, the wheel 80 is fixed to the handle 30 for rotational movement. The wheel 80 may be moved by a thumb of a user to rotate relative to the handle 30, about the longitudinal axis of the wheel 80. The valve seat 88 is also fixedly secured to the handle 30. By way of such an arrangement, and because of the engagement between the gear 82 and the pinion 84, rotation of the wheel 80 will cause the pin 86 to move in or out of a recess 90 in the valve seat 88. In particular, rotation of the wheel 80 in the direction indicated by the arrow F in FIG. 12 will retrieve the pin 86 from the recess 90, whereas rotation of the wheel 80 in the direction indicated by the arrow R in FIG. 13 will insert the pin 86 further into the recess 90.

The valve seat 88 is made of a thermoplastic elastomer (TPE) or silicone, and when the pin 86 is fully received within the recess 90, the valve seat 88 is fully sealed, whereas air may enter the valve seat 88 if the pin 86 is retrieved from the valve seat 88, and the amount of air allowed to enter the valve seat 88 will depend on the extent to which the pin 86 is retrieved from the valve seat 88. The recess 90 is in fluid communication with a nozzle 92, which is in turn in fluid communication with the hood 12, e.g. via a hose (not shown) connected to the conduit 72, so that the pressure within the hood 12 when such is applied over a breast of a user may be fine-tuned by the user by manually operating the wheel 80.

When the breast pump 10 is fitted over a breast of a user and the pump motor 42 is activated, the pump diaphragm 44 will reciprocate to generate a lower pressure ("vacuum") in the hood 12, thus stimulating milk ejection reflex and subsequent expression of milk. Milk from the breast of the user will flow into the hood 12 and subsequently into the chamber 37 in the direction of the arrow M. The milk will accumulate in the chamber 37, first blocking the transmission of infrared signals between the transmitter and receiver of the lower IR unit 38*a*, and subsequently that between the transmitter and receiver of the upper IR unit 38*b*.

In the valve seat 20 is a one-way valve 96 which allows milk to enter the bottle 18, but not vice versa. Because the hood 12 is at a lower pressure than the bottle 18 during operation of the pumping action of the diaphragm 44, the higher pressure in the bottle 18 will prevent the milk in the chamber 37 from entering the bottle 18, thus allowing the milk level to rise in the chamber 37. It may take several sucking/releasing cycles before the milk level rises to, and blocks the transmission of infrared signals between the transmitter and receiver of, the upper IR unit 38*b*. When the milk level rises to the upper IR unit 38*b*, the motor 42 will stop, thus releasing the "vacuum" in the hood 12, in the manner discussed above. In addition, the needle valve 48 will be opened by the valve motor 46, whereby air will exit the bottle 18 via the nozzle 50, and subsequently out of the needle valve 48. The milk in the chamber 37 will thus fall, on its own weight, through the one-way valve 96 into the bottle 18, during the course of which the level of milk in the chamber 37 will fall. The transmission of IR signals between the transmitter and receiver of the upper IR unit 38*b* will thus resume, and then that between the transmitter and receiver of the lower IR unit 38*a* will resume.

Figure 14:
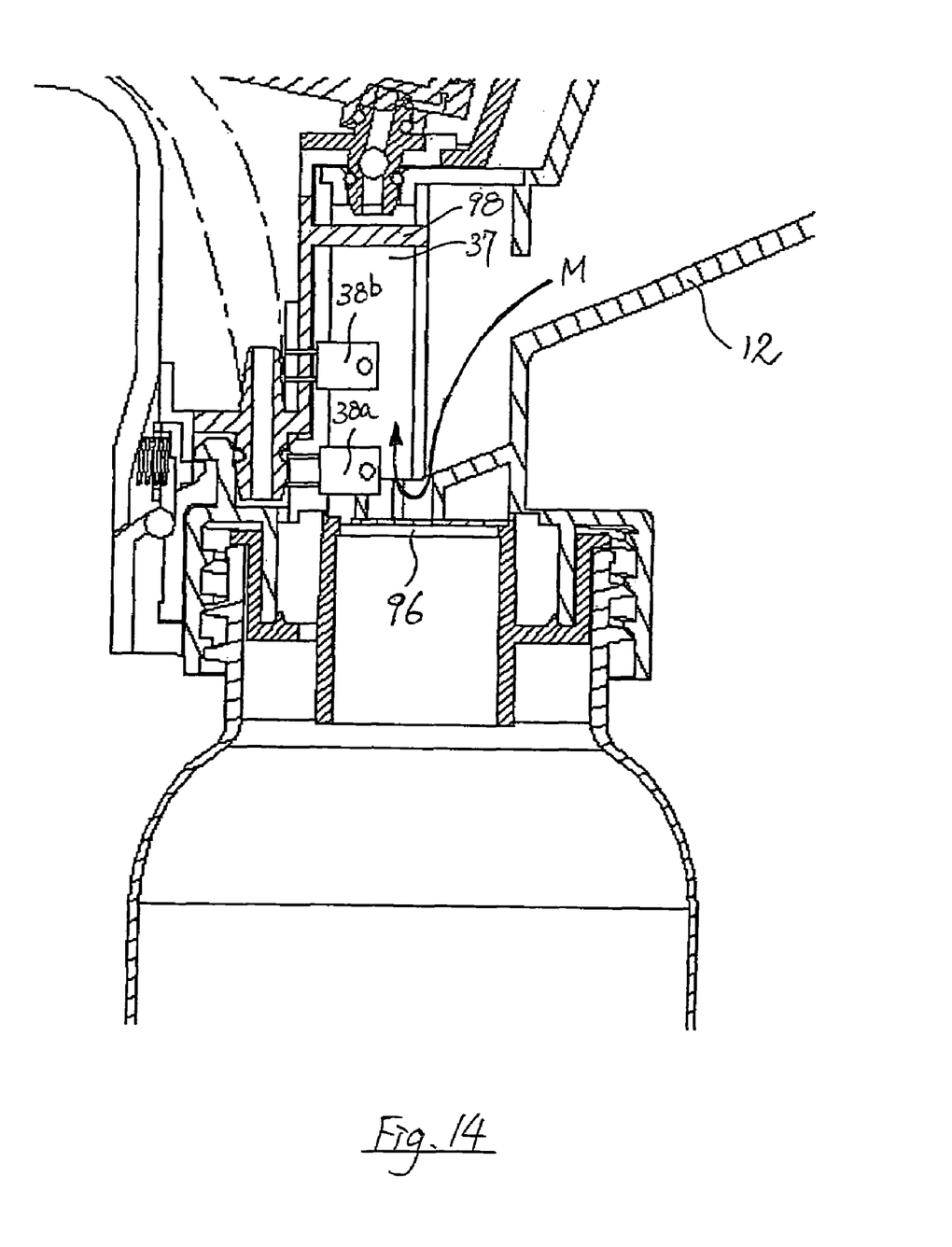
FIG. 14 shows an enlarged sectional view of the milk flow sensing mechanism in the breast pump shown in FIG. 1.

As shown clearly in FIGS. 4 and 14, above the upper IR unit 38*b* is a partition 98 which prevents milk from entering the interior of the head portion 22, e.g. when the breast pump 10 is accidentally knocked over. Milk entering the interior of the head portion 22 may damage the movement parts of the breast pump 10, thus shortening its useful life, or necessitating servicing.

Researches indicate that a baby's feeding is not a single continuous process, but rather a two-phased process in which the baby will initially suckle rapidly, called "stimulation". Once the breast has been sufficiently stimulated, milk begins flowing and the baby will settle into a slower, more relaxed sucking speed for the actual feeding phase, called "expression". The breast pump 10 can mimic the natural feeding pattern of a baby by first exhibiting rapid sucking/releasing actions to stimulate the milk ejection reflex (MER) or "let down". Once milk begins to flow, the breast pump 10 will then exhibit slower and longer sucking/releasing actions which help to maximize milk flow in less time.

Figure 15:
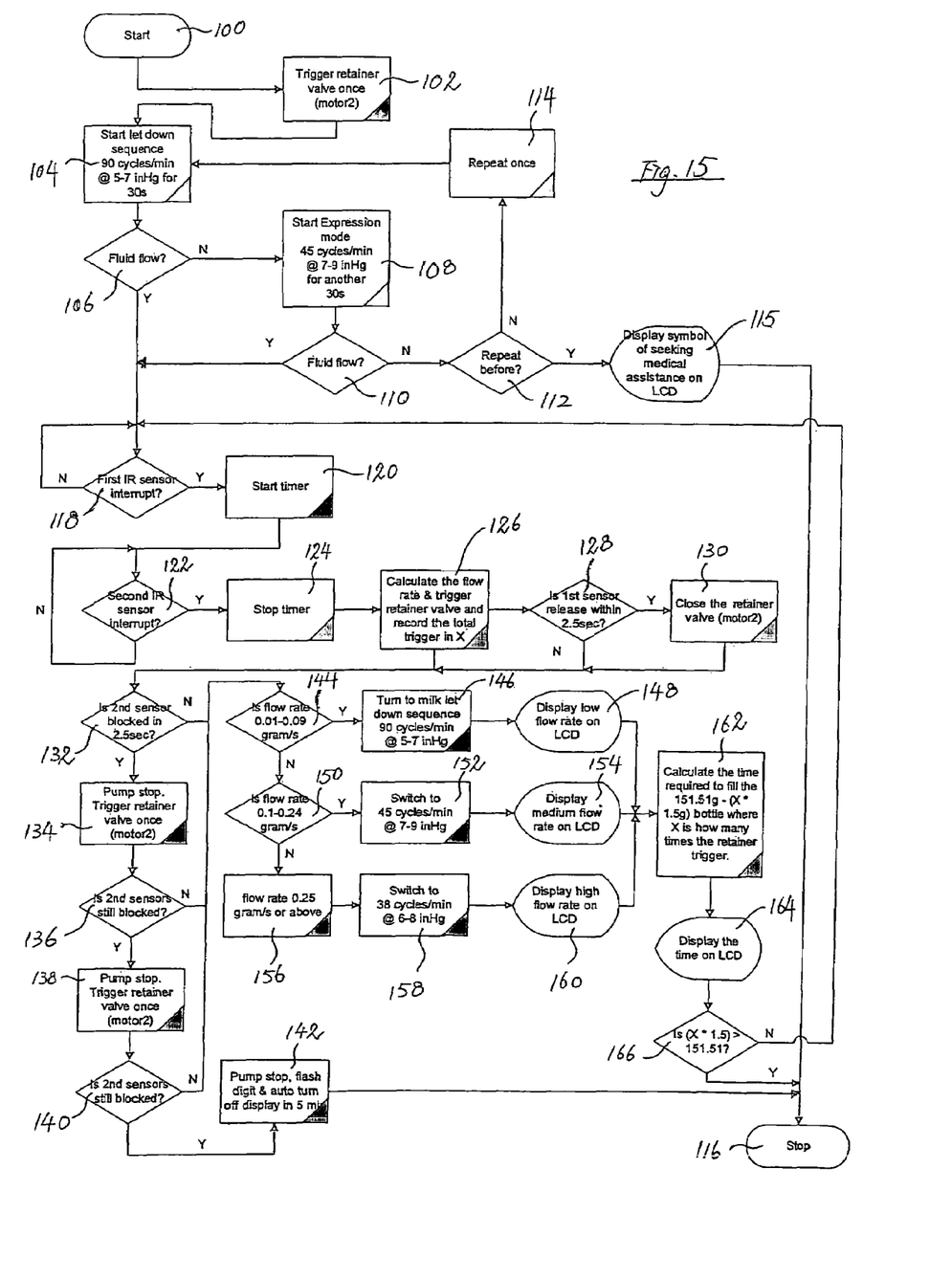
FIG. 15 is a flow chart showing the steps of operation of the breast pump shown in FIG. 1.

The manner of operation of the breast pump 10 will be further discussed by reference to FIG. 15, which shows a flow,v chart of the steps of operation of the breast pump 10. Once the breast pump 10 is started (Step 100), the valve motor 46 will be triggered once to close the needle valve 48, which is called "retainer valve" in FIG. 15 (Step 102). A "let down" sequence will be operated in which sucking/releasing actions will be carried out at a speed of 90 cycles per minute at a pressure of 5-7 inch mercury (in Hg) for 30 seconds (Step 104). If no milk flows (Step 106), an "expression" mode will be operated in which sucking/releasing actions will be carried out at a speed of 45 cycles per minute at a pressure of 7-9 in Hg for 30 seconds (Step 108). If there is still no milk flow (Step 110), the microcontroller 40 of the breast pump 10 (hereinafter simply referred to as the "breast pump 10" for simplicity) will determine if this is the first time such occurs since the breast pump 10 is started (Step 112). If not, the breast pump 10 will repeat the above process (Step 114) by carrying out the "let down" sequence again (Step 104). If, however, such a situation has already occurred once in this operation, a sign or symbol alerting the user to seek medical assistance, e.g. to undergo certain milk flow stimulation operation, will be displayed on the LCD display 28 (Step 115), and the breast pump 10 will also cease operation immediately (Step 116). For carrying out sucking/releasing actions at a frequency of 45 cycles per minute, the pump motor 42 may be activated for 0.8 second, then deactivated for 0.53 second, and then activated for 0.8 second, and so on.

If milk flows after the "let down" sequence (Step 104) or the "expression" sequence (Step 110), the breast pump 10 will then check whether transmission of IR signals in the lower IR unit 38*a* is interrupted (Step 118). If so, a timer in the microcontroller 40 will start timing (Step 120). The breast pump 10 will then check whether transmission of IR signals in the upper IR unit 38*b* is interrupted (Step 122). If so, the timer will stop (Step 124). Because the volume in the chamber 37 between the lower IR unit 38*a* and the upper IR unit 38*b* is known, it is possible to thus calculate the rate of flow of milk (in grams per second, g/s) and such is calculated. The valve motor 46 will be triggered once to open the needle valve 48, thus allowing milk in the chamber 37 to fall into the bottle 18. The breast pump 10 will also count the number of times of such triggers of the valve motor 46 as "X" (Step 126).

The breast pump 10 will then check whether transmission of IR signals in the lower IR unit 38*a* resumes ("released") within 2.5 seconds (Step 128). If so, the valve motor 46 will be triggered once to close the needle valve 48 (Step 130). If transmission of IR signals in the lowver IR unit 38*a* does not resume ("released") within 2.5 seconds (Step 128), or after the closing of the needle valve 48 (Step 130), the breast pump 10 will then check if transmission of IR signals in the upper IR unit 38*b* is still blocked in 2.5 seconds (Step 132). If so, the pump motor 42 will stop operation, and the needle valve 48 will be opened once again (Step 134). If transmission of IR signals in the upper IR unit 38*b* is still blocked (Step 136), the pump motor 42 will stop operation again, and the needle valve 48 will be opened once again (Step 138). If transmission of IR signals in the upper IR unit 38*b* is still blocked (Step 140), the pump motor 42 will stop, a warning signal will be given on the LCD display 28, and the LCD display 28 will be turned off automatically in 5 minutes, (Step 142), and the operation of the breast pump 10 will also stop automatically (Step 116). Such will prevent the motor 42 from continuing operation when, e.g. the breast pump 10 accidentally topples over.

If transmission of IR signals in the upper IR unit 38*b* is not blocked after Step 132, Step 136 or Step 140, the breast pump 10 will operate according to the milk flow rate obtained in Step 126. If the flow rate is between 0.01 to 0.09 g/s (Step 144), the breast pump 10 will switch to "let down" sequence (Step 146) in which sucking/releasing action is carried out at a frequency of 90 cycles per minute at a pressure of 5-7 in Hg, and a sign or symbol indicating low flow rate will be displayed on the LCD display 28 (Step 148). If the flow rate is between 0.1 to 0.24 g/s (Step 150), the breast pump 10 will carry out sucking/releasing action at a frequency of 45 cycles per minute at a pressure of 7-9 in Hg (Step 152), and a sign or symbol indicating medium flow rate will be displayed on the LCD display 28 (Step 154). If the flow rate is 0.25 g/s or above (Step 156), the breast pump 10 will carry out sucking/releasing action at a frequency of 38 cycles per minute at a pressure of 6-8 in Hg (Step 158), and a sign or symbol indicating high flow rate will be displayed on the LCD display 28 (Step 160).

According to the present example, the bottle 18 is designed to hold 151.51 g of milk, and in each cycle, the milk that enters, and is thus collected by, the bottle 18 is 1.5 g. Based on such information, and the frequency at which sucking/releasing action is carried out, the breast pump 10 is able to calculate and display the remaining time required to fill the bottle 18. In this example, it normally requires 101 triggers of the valve motor 46, "X", to fill the bottle 18. Depending on the number of times, "X", the valve motor 46 has already been triggered to open the needle valve 48, the breast pump 10 can calculate the remaining time required for filling up the bottle 18 (Step 162). The remaining time required will be displayed on the TCD display 28 (Step 164).

If 1.5X>151.51 (Step 166), it means that the bottle 18 is filled up, the breast pump 10 will stop (Step 116). If not, the breast pump 10 will check again if transmission of IR signals in the lower IR unit 38a is interrupted (Step 118), and the pumping action will go on again.

It should be understood that the above only illustrates an example whereby the present invention may be carried out, and that various modifications and/or alterations may be made thereto without departing from the spirit of the invention. For example, although the present invention is here described in the context of a "one-pump" model, it is equally applicable to a "two-pump" model, in which a second breast pump is pneumatically connected with the first pump to share in the suction vacuum generated by the pump motor.

It should also be understood that certain features of the invention, which are, for clarity, described in the context of separate embodiments, may be provided in combination in a single embodiment. Conversely, various features of the invention which are, for brevity, described in the context of a single embodiment, may also be provided separately or in any appropriate sub-combinations.

What is claimed is:

1. An electric breast pump comprising:
   at least one hood member adapted to be filled over a breast of a user;
   a chamber in air communication with said hood member via a first valve;
   a first motor;
   a pumping member movable by said first motor to draw air from said hood member into said chamber via said first valve;
   a milk-receiving bottle in liquid communication with said hood member; and
   a second valve in air communication with said bottle,
   wherein said chamber has at least a first opening and a closure member which is movable by said first motor between a first position to close said first opening and a second position in which said first opening is open; and
   wherein said closure member remains at said first position when said first motor is in operation and remains at said second position when said first motor is not in operation.

2. A breast pump according to claim 1 wherein said closure member is biased towards said second position.

3. A breast pump according to claim 2 wherein said closure member is biased towards said second position by a spring member.

4. A breast pump according to claim 1 wherein said first valve is a one-way valve.

5. A breast pump according to claim 1 wherein said first motor is engaged with said closure member via at least one ring-shaped structure.

6. A breast pump according to claim 5 wherein said ring-shaped structure is movable between a stable first configuration to which said ring-shaped structure is biased and a second configuration in which said closure member is allowed to occupy said first position.

7. A breast pump according to claim 5 wherein said ring-shaped structure is at said stable first configuration when said first motor is not in operation and at said second configuration when said first motor is in operation.

8. A breast pump according to claim 7 wherein said ring-shaped structure rotates when said first motor is in operation.

9. A breast pump according to claim 8 wherein said ring-shaped structure moves from said first configuration to said second configuration by centrifugal force when said ring-shaped structure rotates.

10. A breast pump according to claim 1 wherein said chamber includes at least a second opening closable by a third valve.

11. A breast pump according to claim 10 wherein said third valve is a one-way valve.

12. A breast pump according to claim 11 wherein said third valve only allows air to exit said chamber.

13. A breast pump according to claim I further including an adjustment member manually operable to adjust the air pressure in said hood member.

14. A breast pump according to claim 13 wherein said adjustment member includes a fourth valve member in air communication with said hood member.

15. A breast pump according to claim 14 wherein said adjustment member further includes a wheel member manually operable to adjust the amount of air allowed to enter the fourth valve.

16. A breast pump according to claim 1 further including a second motor for selectively opening or closing said second valve.

17. A breast pump according to claim 1 further including at least one sensing unit adapted to detect the passing of milk.

18. A breast pump according to claim 17 further including a data processing unit adapted to calculate the rate of flow of milk on the basis of data received from said sensing unit.

19. A breast pump according to claim 18 wherein said data processing unit is adapted to calculate the remaining time required for filling a receptacle of milk associated with said breast pump.

20. A breast pump according to claim 18 wherein the frequency of movement of said pumping member is adapted to be varied on the basis of the rate of flow of milk calculated by said data processing unit.

21. A breast pump according to claim 17 wherein said sensing unit includes at least one infrared (IR) transmitter and an IR receiver adapted to receive IR signals from said IR transmitter.

22. A breast pump according to claim 21 wherein IR signals transmitted by said IR transmitter are prevented from being received by said IR receiver upon passing of milk therebetween.

23. A breast pump according to claim 22 wherein said first motor is adapted to stop operation when IR signals transmitted by said IR transmitter are prevented from being received by said IR receiver for a predetermined period of time.

24. A breast pump according to claim 17 further including at least a second sensing unit.

25. A breast pump according to claim 24 wherein said first and second sensing units are arranged in series in the path of flow of milk in said breast pump.

26. A breast pump according to claim 25 further including a timer for determining the time duration between when passing of milk is detected by said first sensing unit and when passing of milk is detected by said second sensing unit.

27. A breast pump according to claim 17 further including a display for visually indicating the general rate of flow of milk into said breast pump.

28. An electric breast pump comprising:
   at least one hood member adapted to be fitted over a breast of a user; and
   a first chamber in air communication with said hood member via a first valve;
   a first motor;
   a pumping member movable by said first motor to draw air from said hood member into said chamber via said first valve;
   a milk-receiving bottle in liquid communication with said hood member;
   a second valve in air communication with said bottle; and
   a second chamber in liquid communication with said hood member and said bottle;
   said second chamber including at least an infrared (IR) unit, said
   IR unit including at least one IR transmitter for transmitting IR signals and at least one IR receiver for receiving said IR signals transmitted by said IR transmitter.

29. An electric breast pump according to claim 28 further including a data processing unit adapted to calculate the rate of flow of milk on the basis of data received from said IR unit.

30. A breast pump according to claim 29 further including a display for visually indicating the general rate of flow of milk into said breast pump.

31. A breast pump according to claim 29 wherein said data processing unit is adapted to calculate the remaining time required for filling said bottle.

32. A breast pump according to claim 29 wherein the frequency of movement of said pumping member is adapted to be varied on the basis of the rate of flow of milk calculated by said data processing unit.

33. A breast pump according to claim 28 further including at least a second IR unit.

34. A breast pump according to claim 33 wherein said first and second IR units are arranged in series in the path of flow of milk in said breast pump.

35. A breast pump according to claim 34 further including a timer for determining the time duration between when passing of milk is detected by said first sensing unit and when passing of milk is detected by said second IR unit.

36. A breast pump according to claim 28 wherein IR signals transmitted by said IR transmitter are prevented from being received by said IR receiver upon passing of milk therebetween.

37. A breast pump according to claim 36 wherein said first motor is adapted to stop operation when IR signals transmitted by said IR transmitter are prevented from being received by said IR receiver for a predetermined period of time.

38. A breast pump according to claim 28 wherein said first valve is a one-way valve.

39. A breast pump according to claim 28 wherein said chamber has at least a first opening and a closure member which is movable by said first motor between a first position to close said first opening and a second position in which said opening is open, and wherein said closure member remains at said first position when said first motor is in operation and remains at said second position when said first motor is not in operation.

40. A breast pump according to claim 39 wherein said closure member is biased towards said second position.

41. A breast pump according to claim 40 wherein said closure member is biased towards said second position by a spring member.

42. A breast pump according to claim 39 wherein said first motor is engaged with said closure member via at least one ring-shaped structure.

43. A breast pump according to claim 42 wherein said ring-shaped structure is movable between a stable first configuration to which said ring-shaped structure is biased and a second configuration in which said closure member is allowed to occupy said first position.

44. A breast pump according to claim 43 wherein said ring-shaped structure is at said stable first configuration when said first motor is not in operation and at said second configuration when said first motor is in operation.

45. A breast pump according to claim 44 wherein said ring-shaped structure rotates when said first motor is in operation.

46. A breast pump according to claim 45 wherein said ring-shaped structure moves from said first configuration to said second configuration by centrifugal force when said ring-shaped structure rotates.

47. A breast pump according to claim 39 further including a second motor for selectively opening or closing said second valve.

48. A breast pump according to claim 28 wherein said first chamber includes at least a second opening closable by a third valve.

49. A breast pump according to claim 48 wherein said third valve is a one-way valve.

50. A breast pump according to claim 49 wherein said third valve only allows air to exit said chamber.

51. A breast pump according to claim 28 further including an adjustment member manually operable to adjust the air pressure in said hood member.

52. A breast pump according to claim 51 wherein said adjustment member includes a fourth valve member in air communication with said hood member.

53. A breast pump according to claim 52 wherein said adjustment member further includes a wheel member manually operable to adjust the amount of air allowed to enter the fourth valve.

54. An electric breast pump including:
   at least one hood member adapted to be fitted over a breast of a user;
   a chamber in air communication with said hood member via a first valve;
   a first motor;
   a pumping member movable by said first motor to draw air from said hood member into said chamber via said first valve;
   a milk-receiving bottle in liquid communication with said hood member; and
   a second valve in air communication with said bottle; and
   a second motor for selectively opening or closing said second valve
   wherein said chamber has at least a first opening and a closure member which is movable by said first motor between a first position to close said first opening and a second position in which said first opening is open; and
   wherein said closure member is at said first position when said first motor is in operation and is at said second position when said first motor is not in operation.

* * * * *